(12) United States Patent
Ales et al.

(10) Patent No.: US 7,581,445 B2
(45) Date of Patent: *Sep. 1, 2009

(54) METHOD FOR ULTRASONIC TESTING OF FITTING ASSEMBLY

(75) Inventors: Richard A. Ales, Mentor, OH (US); William H. Glime, Painesville, OH (US); John Barry Hull, Leicestershire (GB); Jeffrey M. Rubinski, Wickliffe, OH (US); Michael Douglas Seymour, Cotgrave (GB); Peter C. Williams, Cleveland Heights, OH (US); Wenxian Yang, Dunkirk (GB)

(73) Assignee: Swagelok Company, Solon, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 11/868,127

(22) Filed: Oct. 5, 2007

(65) Prior Publication Data

US 2008/0022772 A1   Jan. 31, 2008

Related U.S. Application Data

(62) Division of application No. 10/518,337, filed as application No. PCT/US03/19133 on Jun. 17, 2003, now Pat. No. 7,284,433.

(60) Provisional application No. 60/389,394, filed on Jun. 17, 2002.

(51) Int. Cl.
  *G01N 29/04* (2006.01)
(52) U.S. Cl. .................. 73/597; 285/93; 73/622
(58) Field of Classification Search ........... 73/597, 73/599, 622, 627; 285/93
  See application file for complete search history.

(56) References Cited

U.S. PATENT DOCUMENTS

| 3,103,373 | A | 9/1963 | Lennon et al. |
| 3,218,845 | A | 11/1965 | Joy |
| 3,287,813 | A | 11/1966 | Lennon et al. |
| 3,325,192 | A | 6/1967 | Sullivan |
| 4,014,208 | A | 3/1977 | Moore et al. |
| 4,127,927 | A | 12/1978 | Hauk et al. |

(Continued)

FOREIGN PATENT DOCUMENTS

| GB | 264762 | 1/1927 |
| GB | 1361372 | 7/1974 |
| GB | 2353342 | 2/2001 |
| WO | 99/31499 | 6/1999 |

OTHER PUBLICATIONS

International Search Report of PCT/US03/18812, mailed Aug. 4, 2004.

(Continued)

*Primary Examiner*—John E Chapman
(74) *Attorney, Agent, or Firm*—Calfee, Halter & Griswold LLP (57) ABSTRACT

Apparatus and method for determining relative and/or absolute axial position of a conduit end within a fluid coupling includes application of input ultrasonic energy in the form of transient shear waves and analyzing the reflected energy. Application of the input energy collected at different radial positions about a first axial location is used with wavelet based correlation techniques to better analyze the reflected energy signals. Quality of the abutment between the conduit end and a surface associated with the coupling may also be determined as a separate or combined feature of the axial position determination.

22 Claims, 4 Drawing Sheets

U.S. PATENT DOCUMENTS

| | | | |
|---|---|---|---|
| 4,233,723 A | 11/1980 | Eshghy |
| 4,365,402 A | 12/1982 | McCombs et al. |
| 4,573,359 A | 3/1986 | Carstensen |
| 4,592,125 A | 6/1986 | Skene |
| 4,614,120 A | 9/1986 | Fradin et al. |
| 4,655,159 A | 4/1987 | McMills |
| 4,700,576 A | 10/1987 | Grare et al. |
| 4,791,816 A | 12/1988 | Grare et al. |
| 4,791,839 A | 12/1988 | Bickford et al. |
| 4,870,866 A | 10/1989 | Slack |
| 4,962,579 A | 10/1990 | Moyer et al. |
| 5,074,599 A | 12/1991 | Wirbel et al. |
| 5,099,437 A | 3/1992 | Weber |
| RE34,063 E | 9/1992 | Vincent et al. |
| 5,233,742 A | 8/1993 | Gray et al. |
| 5,280,967 A | 1/1994 | Varrin et al. |
| 5,321,506 A | 6/1994 | Sargent |
| 5,499,540 A | 3/1996 | Whaley et al. |
| 5,535,136 A | 7/1996 | Standifer |
| 5,719,785 A | 2/1998 | Standifer |
| 5,807,048 A | 9/1998 | d'Agraives et al. |
| 5,884,232 A | 3/1999 | Buder |
| 6,279,242 B1 | 8/2001 | Williams et al. |
| 6,301,512 B1 | 10/2001 | Motzer |
| 6,327,912 B2 | 12/2001 | Basile et al. |
| 6,345,845 B2 | 2/2002 | Johnston |
| 6,360,609 B1 | 3/2002 | Wooh |
| 6,397,679 B1 | 6/2002 | Sakok et al. |
| 6,438,814 B1 | 8/2002 | Seymour et al. |
| 6,578,422 B2 * | 6/2003 | Lam et al. ............ 73/622 |

OTHER PUBLICATIONS

International Search Report of PCT/US03/19133, mailed Jul. 14, 2004.

Article "Investigation of Signal Characteristics Using the Continuous Wavelet Transform", John Sadowsky, pp. 258-269, Johns Hopkins APL Technical Digest, vol. 17, No. 3, 1996.

Article "Ultraschallprufung Grundlagen und industrielle Anwendungen", Deutsch V. et al. pp. 55-73, 1997, XP002279058 Berlin Heidelberg New York.

* cited by examiner

METHOD FOR ULTRASONIC TESTING OF FITTING ASSEMBLY

RELATED APPLICATION

The present application is a divisional of pending U.S. Ser. No. 10/518,337 filed on Dec. 15, 2004, for ULTRASONIC TESTING OF FITTING ASSEMBLY FOR FLUID CONDUITS WITH A HAND-HELD APPARATUS, which is a national phase entry under 35 U.S.C. §371 and claims priority to International Application No. PCT/US2003/19133, with an International Filing Date of Jun. 17, 2003, for ULTRASONIC TESTING OF FITTING ASSEMBLY, which claims the benefit of U.S. Provisional Patent Application Ser. No. 60/389,394, filed on Jun. 17, 2002, for ULTRASONIC FITTING ASSEMBLY VALIDATION, which are all fully incorporated by reference herein.

TECHNICAL FIELD OF THE INVENTION

The invention relates generally to apparatus and methods for non-destructive evaluation of fitting assemblies after assembly is completed. More particularly, the invention relates to using mechanical energy to make evaluations of the fitting assembly.

BACKGROUND OF THE INVENTION

Fluid handling equipment, whether the fluid is gas, liquid, combination of gas and liquid, slurries and so on, may use many fluid control devices that are connected together with the use of fittings. Typical fluid control devices include valves, regulators, meters and so on that are interconnected in a fluid circuit with either tube or pipe. The fittings may take on a wide variety of designs, including but not limited to single ferrule and multi-ferrule tube fittings, various clamping arrangements using elastomeric seals, gripping rings and so on. For purposes of this disclosure we refer to tube and pipe as "conduit" because the present invention may be used with either tube or pipe.

Common to nearly all fluid circuits that use fittings to connect conduit to a flow control device or process is the desire to verify in a non-destructive manner that a fitting has been fully assembled. Most connections via fittings involve the positioning of a conduit within a fitting body or other structure associated with a fluid coupling (referred to herein as a fitting assembly of a conduit and coupling) such that an end of the conduit abuts a shoulder or wall of the fitting body or other structure. This abutment or "bottoming" as we also refer to it herein, is usually desirable as it allows that gripping device, such as a ferrule, to be installed onto the conduit without the conduit moving axially.

Inherent in the assembly process, however, is the practical circumstance that once the fitting is installed there is no cost-effective non-destructive way, known to date, to determine that the conduit is fully bottomed. For example, it is known to use x-rays to observe the fitting condition, however, this is a very expensive process and simply not practical for many if not most assemblers. Various techniques are known that are used to verify proper installation of the fitting components, or to verify proper pull-up based on the number of turns of a fitting nut or axial displacement of the conduit relative to the nut. For example, the fitting may be disassembled after pull-up, visually inspected and then reassembled, but such steps are time consuming and costly. In another known technique, the tubing may be pre-marked in an appropriate manner prior to assembly, but this technique is subject to error in the marking or interpretation process. None of these techniques can absolutely determine in a final assembled fitting that the conduit is bottomed, and also determine the nature or quality of the contact or abutment between the conduit and the associated structure.

The need exists therefore to provide process and apparatus for non-destructive analysis and evaluation of whether a conduit is properly bottomed within a fitting.

SUMMARY OF THE INVENTION

The invention contemplates in one aspect determining position of a conduit end using input energy applied to the conduit. In one exemplary embodiment, ultrasonic energy emitted from a shear wave transducer is applied to the conduit and propagates through the conduit as mechanical waves. Alternatively or in combination, the input energy may be applied through one or more of the fluid coupling components such as the fitting body, for example. Reflected energy (also sometimes referred to herein alternatively as return signals, return energy, return energy signals, reflected signals or reflected energy signals) is converted into electrical signals by the transducer and these electrical signals are analyzed to determine position of the conduit end. In a specific exemplary application the invention may be used to determine the position of an end of the conduit within a fluid coupling installed thereon. In alternative applications, the invention may be used to determine proper assembly of one or more of the ferrules in a single or multi-ferrule tube fitting by detecting a characteristic of the tube bite or indentation typically associated with ferrule-type tube fittings, such as, for example, the axial location thereof or the presence/absence thereof.

In accordance with another aspect of the invention, correlation techniques are used to more clearly discriminate the reflected energy signals. In one exemplary embodiment, ultrasonic energy is applied to the conduit at different radial positions about a first location of the conduit that is axially spaced from the conduit end. Reflected energy signals are correlated to determine relative axial position of the conduit end. Noise reduction may also be applied to the return signals.

In accordance with another aspect of the invention, the quality and/or nature of contact between the conduit and a surface associated with a fluid coupling installed on the conduit end may be determined. In one exemplary embodiment, ultrasonic energy is applied to the conduit and the amplitude of reflected energy is analyzed to determine the quality of the contact or bottoming of the conduit end against the surface associated with the fluid coupling, such as, for example, whether the conduit end is fully bottomed, partially bottomed or not bottomed. Correlation analysis may also be used in connection with this aspect of the invention.

In another embodiment of the invention, a tool is provided that integrates a source that applies mechanical energy waves, an analyzer that determines the characteristics of a fitting assembly as a function of reflected portions of energy waves, or both, with a gap gauge.

These and other aspects and advantages of the present invention will be readily appreciated and understood from the following detailed description of the invention in view of the accompanying drawings.

DETAILED DESCRIPTION OF THE INVENTION

1. Introduction

The present invention is directed to apparatus and methods relating to determining position of a conduit within a fluid coupling installed on the conduit. This determination may include, separately or combined, determining the axial position of an end of the conduit within a fluid coupling, and determining the quality of contact between the conduit and a surface associated with the fluid coupling.

Determining the axial position of a conduit within a fluid coupling is particularly useful, for example, with tube fittings of the type that have a threadably coupled nut and body and at least one ferrule that is used to provide a fluid tight coupling between the tube end and the body. Although the invention is described herein with particular reference to its use with a two ferrule flareless tube fitting, those skilled in the art will readily appreciate that the invention may be used in many other applications, and generally to any application wherein it is desired to determine the relative and/or absolute axial position of an end of a conduit, such as tubing or pipe, whether the conduit end is positioned with a fluid coupling, a fluid flow device or so on.

Determining the nature or quality of contact is also particularly useful, for example, with the aforementioned tube fittings. In particular, the fitting body includes a generally radial shoulder against which the tube end is preferably abutted after a complete pull-up of the fitting. By "pull-up" is simply meant the final assembly and tightening of the coupling nut (beyond the initial finger tight assembly) and body so as to secure the one or more ferrules onto the tube end in a seal-tight manner. The quality of this abutting relationship is affected by many factors, including but not limited to, the facing operation of the tube end, such as the degree of flatness and square alignment of the tube end, the nature of the radial shoulder in the body including its flatness and square alignment, the amount of tube deformation that may occur during pull-up, the amount of compressive load between the tube end and the body shoulder, and so on. The quality of the bottoming is therefore a general reference to the completeness of the bottoming and the load between the abutting surfaces, as exhibited by the nature of the contact in terms of the amount of contact area, the characteristics of the abutting surfaces and so on. The particular characteristics of quality and nature of the abutment may be selected as required for a particular application. Again, the invention will find application beyond two ferrule flareless tube fittings, and may be used in many applications wherein it is desired to determine the quality of the abutment between a conduit end and a surface in a fluid element such as a tube fitting, a flow control device and so on. In many coupling applications, simply knowing the quality of the conduit end insertion, for example whether the conduit end is fully bottomed, partially bottomed or not bottomed, is the most useful information, regardless of the ability to detect axial position of the conduit end.

In the exemplary embodiments herein, the invention is realized using ultrasonic energy as an input energy signal. The more specific, but not necessarily required, characteristics of the ultrasonic energy in the exemplary embodiments is ultrasonic energy in the form of a generally continuous mechanical wave or waves having one or more discontinuities. In other words, the input energy may be applied as a series of one or more transient waveforms. The input energy signal in the exemplary embodiments therefore is in the form of one or more packets or pulses of the energy waveform. By "pulse" or "packet" we do not intend to restrict the waveform of the input signal to any particular or required waveform shape or characteristic either in the time, frequency, wavelength or amplitude domains. In the exemplary embodiments, the input energy signal is realized in the form of a transient signal having one or more harmonic waveforms with decreasing amplitudes over the time duration of the transient signal. The input waveform characteristics may be selected to facilitate analysis of the return signals, such as by the correlation techniques described herein. Alternatively, the applied waveform may be any Fourier series waveform for example, including an impulse harmonic waveform, a square wave, and so on. Those skilled in the art will appreciate that the invention may be used with any conveniently available form of reflectable mechanical energy, as distinguished from electromagnetic energy such as x-rays, that is transmitted by pressure waves in a material medium, such as, for example, the conduit or one or more parts of a fluid coupling, and detected therefrom.

While the invention is described and illustrated herein with particular reference to various specific forms and functions and steps of the apparatus and methods thereof, it is to be understood that such illustrations and explanations are intended to be exemplary in nature and should not be construed in a limiting sense. For example, the present invention may be utilized with any fluid coupling between a conduit and a fluid flow member including but not limited to another conduit. The term fluid coupling therefore is used in its broadest sense to refer to any mechanical connection between a conduit end and an abutment surface of another fluid flow element. Furthermore, while the invention is described herein with reference to stainless steel tubing and tube fittings, the invention will find application with many other metals and indeed non-metal applications such as plastics, as well as to tubing, pipe and so on.

Additionally, various aspects of the invention are described herein and are illustrated as embodied in various combinations in the exemplary embodiments. These various aspects however may be realized in alternative embodiments either alone or in various other combinations thereof. Some of these alternative embodiments may be described herein but such descriptions are not intended to be a complete or exhaustive list of available alternative embodiments or modifications. Those skilled in the art may readily adopt one or more of the aspects of the invention into additional embodiments within the scope of the present invention even if such embodiments are not expressly disclosed herein. Additionally, even though some features and aspects and combinations thereof may be described herein as having a preferred form, function, arrangement or method, such description is not intended to suggest that such preferred description is required or necessary unless so expressly stated. Those skilled in the art will readily appreciate that the invention may be used with additional modifications, improvements and equivalents either known or later developed as substitute or alternatives for the embodiments described herein.

2. Detailed Description of Embodiments of the Invention

Figure 1:
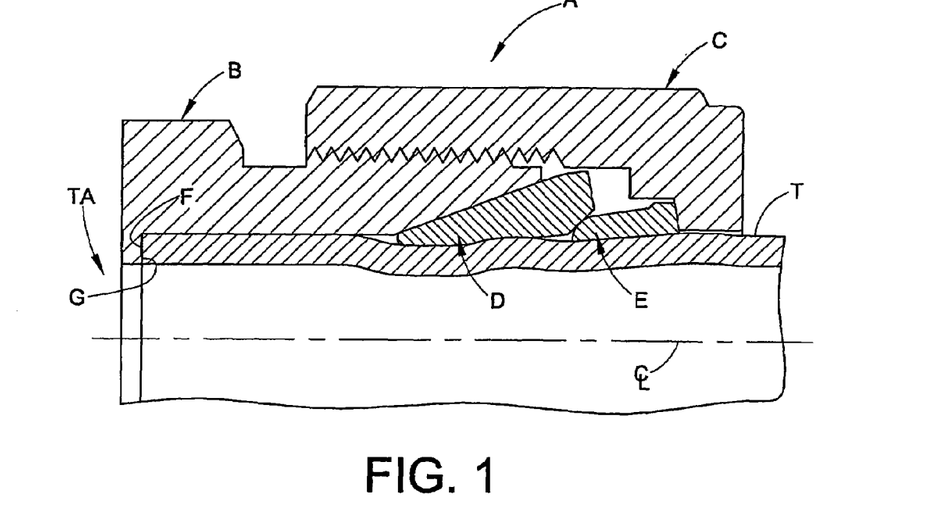
FIG. 1 is a prior art two ferrule flareless tube fitting as an exemplary fluid coupling that the present invention may be used with, illustrated in half-view longitudinal cross-section.

With reference to FIG. 1, there is illustrated a highly successful two ferrule tube fitting A. This fitting A is described in U.S. Pat. No. 3,103,373 owned by the assignee of the present invention and fully incorporated herein by reference. The illustration of FIG. 1 shows only one half of the fitting, it being recognized by those skilled in the art that the other half of the view is identical about the centerline CL.

The fitting A includes a body B, a nut C that is threadably engaged with the body B during finger-tight assembly and pull-up, a front ferrule D and a back ferrule E. The fitting A is illustrated installed on a conduit, in this case in the form of a tube end T. The tubing T may carry a media such as liquid, gas, slurry and so on. The assembly in FIG. 1 is illustrated in the pulled-up condition, with the ferrules D and E plastically deformed so as to provide a fluid tight seal and strong grip on the tube end T.

It is desirable that the inner end F of the tube end T abut at the region TA defined at a radial shoulder G formed in the body B. This abutment is referred to as "bottoming" the tube end T and is desirable to provide a strong mechanical assemblage, including forming a good seal and having a strong tube grip, that can withstand environmental conditions such as temperature variations and vibration effects. A seal may but need not be formed at the abutment between the surfaces F and G. Whether a seal is formed there or not, it would be advantageous to be able to determine that the tube end is bottomed and the quality, nature or completeness of the contact. A tube end could be partially or incompletely bottomed by virtue of the assembler failing to properly insert the tube end sufficiently into the body B in accordance with the manufacturer's instructions.

A fully bottomed conduit end would be a condition in which there was substantial surface to surface contact between the conduit end and the body shoulder and good solid mechanical contact or compression therebetween. A partially bottomed conduit end would be a condition in which, for example, there is not substantial surface to surface contact due to poor end facing of the conduit end, a cocked or tilted conduit, or simply a lack of strong compression between the two abutting surfaces. A conduit end that is not bottomed would be a condition of little or no surface to surface contact or the presence of an actual axial gap between the non-abutting surfaces. Therefore, as used herein, the nature or quality of the contact between the conduit end and the abutting surface refers generally but not exclusively to various features either alone or in various combinations including the amount of surface area where contact is made, the force or load between the conduit end and the abutting surface, presence of a gap therebetween, lack of square alignment of the abutting surfaces, and so on.

Figure 2:
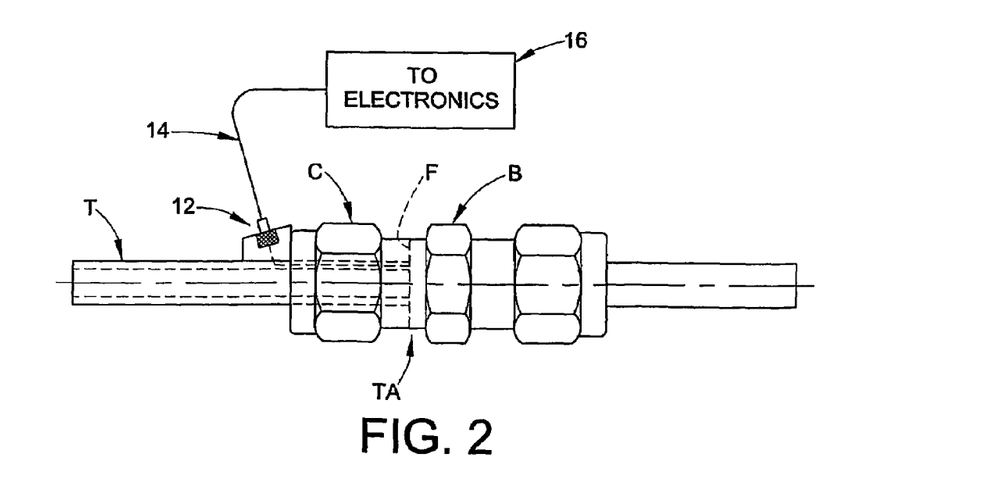
FIG. 2 is an elevation of a fluid coupling assembly and the present invention.

With reference to FIG. 2 we illustrate a first embodiment of the invention. An input energy source or input device 12 is coupled to the conduit T so as to apply mechanical input energy into the conduit T, wherein a portion of the applied input energy is reflected back or returned. The source device 12 may be, for example, a transducer that converts an electrical drive signal into vibration or mechanical energy. One example is an ultrasonic transducer that emits a high frequency signal which may be reflected or otherwise returned to the source 12 by a variety of conditions including but not limited to inclusions, micro-structural deformations, voids, the tube end F, and tubing deformations or indentations such as the ferrule bite or compression. The source 12 is used as a transmitter as well as a receiver or sensor and converts the reflected energy that reaches the source 12 into a corresponding electrical signal. Alternatively, the transmitter and receiver may be separate or different devices. The source 12 is coupled via a cable 14 or other suitable connection to an electronics arrangement 16. The electronics 16 includes appropriate circuitry that generates the drive signal for the source device 12 and that receives the electrical signals from the source device 12.

We have found that—although a surface wave transducer or a delay line transducer may be used to determine the bottomed condition of a tube end, as well as proper assembly of the tube fitting, and that either of these transducers is a useful alternative to the exemplary embodiment herein—a preferred technique and device is to use a shear wave transducer to apply the input energy to the conduit T. A shear wave transducer is distinguished from a delay line transducer in that the shear wave transducer applies energy into an object generally longitudinally or along the direction of the surface of the object, whereas a delay line transducer applies energy generally normal to the surface, and thus may be used to determine wall thickness. The shear wave transducer is thus able to produce a better return reflection or echo of the end of the conduit, particularly when the conduit is only partially bottomed or completely not bottomed.

A suitable and exemplary transducer is a Phoenix-ISL shear wave transducer model SSW-4-70 that is resonant at 4 Megahertz. Other transducers commercially available or later developed will also be suitable for the present invention, and the invention is not limited to the use of ultrasonic energy waves. Non-ultrasonic wave frequencies may be used provided that adequate and detectable energy is reflected back from the tube end. It is also possible to use a tuned frequency that provides the strongest echo from the conduit end depending on the conduit dimensions, material, temperature, the fluid coupling associated therewith, and so on.

It is worth noting at this time that a particular advantage of the present invention is that it may be used to determine the bottoming condition of a conduit within a fluid coupling in a non-destructive manner, even while the fluid is present in the conduit. Thus there is no need to necessarily purge the system or disassemble any components, although such may be desirable in some circumstances.

We have further found that easily interpreted data can be obtained after noise filtering and performing correlation analysis to the reflected energy. We have moreover found that a Morlet wavelet function, well known to those skilled in the art as to its mathematical form, aids the filtering function with the invention, however, the present invention is not limited to using such a Morlet wavelet function. For example, other types of exponential sinusoidal wavelet functions, or other filtering functions, may be alternatively useful in some applications.

Figure 3:
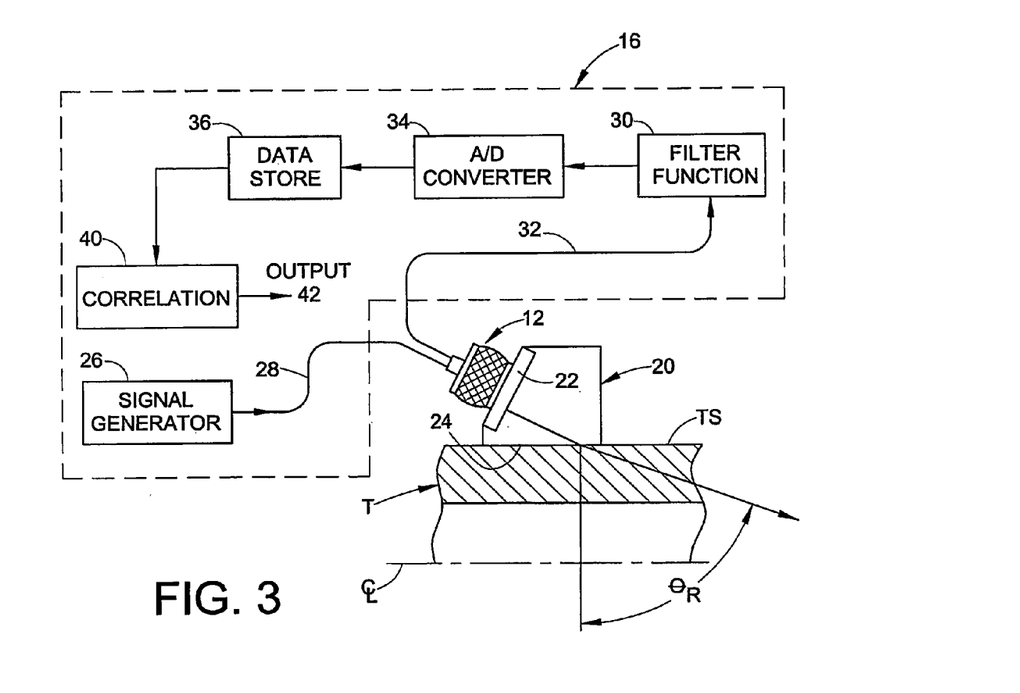
FIG. 3 is a functional block diagram of an analyzer in accordance with the invention.

With reference to FIG. 3, we illustrate a detailed functional block diagram of the electronics arrangement 16 in the form of an analyzer. It is desirable that the invention be realized in the digital analysis domain, however, such is not required and it may be suitable in some applications to perform analog or hybrid analog/digital analysis.

FIG. 3 also illustrates additional aspects of the invention relating to the mounting of the source 12. In this example, the source 12 is a shear wave transducer and is firmly supported on a base 20 that can be suitably attached to or placed in contact with the conduit surface TS. The base 20 preferably is made of a high transmission material, such as acrylic resin, so that the energy emitted from the transducer face 22 is coupled with good efficiency into the conduit T. The use of a base 20 or other suitable structure enhances the coupling because the base 20 can be provided with a surface 24 that conforms to the surface profile of the conduit surface TS. This usually will be an improvement over simply trying to position the typically flat transducer face 22 against a cylindrical surface TS, however, in some applications, especially large diameter conduits, such a direct mounting may be useable. A suitable low attenuation coupling material may also be applied between the base surface 24 and the conduit surface TS. A suitable low attenuation liquid couplant may be water for example, however other coupling material such as solid or paste may be used, such as for example, latex or silicone rubber or AQUALENE™ available from R/D Tech. The use of a coupling material may be omitted in cases where the signal coupling between the conduit and the transducer does not adversely attenuate either the drive signal into the conduit or the reflected energy back into the transducer.

FIG. 3 illustrates that the base 20 may be configured so that the transducer face 22 is angled away from normal towards the conduit longitudinal axis CL. In this manner, the input energy enters the conduit structure at an angle $\theta_R$. We have found that a suitable range for $\theta_R$ is from about greater than 0° to about 90°, more preferably about 45° to about 85°, and most preferably about 65° to about 75°. However, the selected angle for $\theta_R$ in any particular application may be selected based on the angle that produces the best or most useful return energy profiles. Materials having appropriate indices of refraction may be selected to allow refraction to assist in the input energy entering the coupling assembly at the desired angle $\theta_R$.

With continued reference to FIG. 3, the analyzer 16 may be realized in the form of any suitable digital processor including but not limited to DSP, microprocessors, discrete digital circuits and so on. The analyzer processor 16 may conveniently be any commercially available or later developed circuit that is programmable in accordance with programming techniques well known to those skilled in the art, to carryout the functions described herein. The analyzer processor 16 thus includes a signal generator 26 that produces a suitable drive signal that is coupled to the transducer 12 via a suitable cable or wire 28. The analyzer processor 16 further includes a filter function 30 that may be used for noise reduction, since the electrical signal from the transducer 12 will typically include a substantial amount of background undesired noise. Any suitable filter design in circuitry or software well known to those skilled in the art may be used. Note that in FIG. 3 the noise filtering function is performed on the analog signal from the transducer 12. Alternatively, digital filtering may be performed in cases when the transducer signal has been digitized. Still further, a filter function may be included in the transducer itself, and special shielding on the cables and transducer assembly may be used as required to further reduce noise.

The filter function 30 receives the electrical output signal from the transducer 12 via a cable or other suitable connection 32 (note that the wire 32 and the wire 28 are part of the aforementioned cable 14 of FIG. 2).

The filtered signal from the transducer 12 is then input to a conventional analog to digital (A/D) converter 34. The A/D converter 34 converts the electrical signal from the transducer 12 into a digitized signal that can be conveniently stored in a storage device such as a memory 36. The memory 36 may be volatile or non-volatile memory or both depending on the type of data analysis to be performed.

In some applications, the reflected energy signal may have a very pronounced and easily discernible signal level that corresponds to the axial position of the conduit end relative to the energy source 12. Note that the axial position of the conduit end relative to the transducer may be determined either as an absolute number or a relative number, and is computed based on knowing the propagation speed of the energy through the conduit, as is well known in the art of ultrasonic analysis. If the reflected energy provides an easily discernible signal stored in the memory 36, then the controller 16 can simply be programmed to determine the characteristics of the signal to ascertain the axial position of the conduit end.

In accordance with another aspect of the invention, the relative strength of the reflected energy is an indication of the quality of the bottoming. We have found that when there is good or complete bottoming, very little energy is returned from the conduit end because the energy passes through into the fitting body material (and/or other contacting structures) and there is thus a substantial attenuation in the reflected or returned energy. Thus interestingly, the absence of a strong reflected energy level actually indicates excellent bottoming. For an un-bottomed conduit end, a high and sharply pronounced reflected energy level is returned due to reflection at the gap interface between the conduit end and the body shoulder. For a partially bottomed conduit end, the reflected energy will be somewhere in between a fully bottomed conduit end and an un-bottomed conduit end. Test samples and empirical data may be used to calibrate the system 16 as required.

We have further found through experimentation, however, that the mechanical complexity of a typical fluid coupling and conduit micro-structure renders a nice clean easy-to-detect reflected energy signal to not be a practical reality. Instead, all sorts of false or non-repeatable echoes may arise. Furthermore, we have found that for a single axial location of the transducer relative to the conduit end, the circumferential position of the transducer may significantly influence the nature of the reflected energy. For example, the reflected energy from the conduit end may not always appear at the same time delay marker when the transducer is moved about different circumferential positions, even at the same axial location, on the conduit. We attribute this to micro-variations in the conduit and the fluid coupling structure, but whatever the causes may be, the practical consequence is that they typically will be present.

Figure 4:
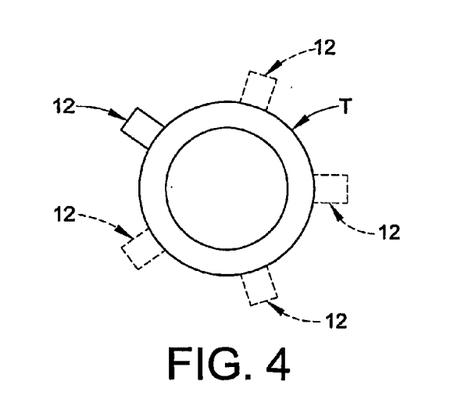
FIG. 4 is an end view of an optional configuration for an ultrasonic transducer location in accordance with another aspect of the invention.

In accordance then with another aspect of the invention, the energy applied into the conduit T is done at two or more circumferential positions about the selected axial location of the source transducer 12. This is illustrated in FIG. 4 wherein reflected energy data is collected and stored for two or more circumferential positions of the source transducer 12 about the conduit at the axial location selected. This can be performed using a plurality of transducers positioned at different positions about the conduit T, or more simply by repositioning a single transducer 12 and then collecting data at each location as indicated by the dashed lines in FIG. 4. The different positions may be but need not be evenly spaced about the conduit.

Each application of input energy at a particular circumferential position produces reflected or return energy that is converted into an electrical signal, filtered and stored as previously described herein. Data is collected for two or more, and preferably about three, different circumferential positions at the selected axial location of the transducer (which in the exemplary embodiment is just behind the nut C of the fitting assembly A.) A correlation function 40 is then applied to the set of data from the plurality of circumferential positions. The correlation analysis substantially eliminates or "filters" the random return energy signals from the micro-variations in the conduit because their positions relative to the applied energy transducer source 12 changes as the transducer is repositioned about the conduit T. The conduit end relative position, however, does not, and correlation analysis distinctly discriminates the corresponding signal. The correlation analysis may be conventional, such as for example but not limited to, the analysis disclosed in *Correlation Analysis of Spatial Time Series Datasets: A Filter and Refine Approach*, Zhang, Huang, Shekhar and Kumar, University of Minnesota, Technical Report Abstracts, 2001, the entire disclosure of which is fully incorporated herein by reference. We have found that the selected signal correlation analysis may be significantly facilitated by optionally but preferably using the wavelet based correlation method disclosed in *Complex Wavelet Analysis of Ultrasonic Signals*, Hull, Yang, and Seymour, to be published in IMechE (Institution of Mechanical Engineers, London), June, 2003, the entire disclosure of which is fully incorporated herein by reference, and which may be implemented/programmed in software or firmware using conventional and well known techniques. The analyzer 16 can thus produce an output 42, in any suitable form including but not limited to a visual output, printed output and so on, of the quality of the conduit end bottoming and, if so desired or alternatively separately desired, the absolute or relative axial position of the conduit end as a function of the axial location of the source 12.

The present invention contemplates not only the structure of the aforementioned apparatus, but also the methods embodied in its use, and furthermore a method for determining position of a conduit end within a fluid coupling and a method for determining the quality of the bottoming of a conduit end against a structural surface. Such a method includes the steps of applying energy into the conduit structure, detecting reflected or returned energy from the conduit end and determining the position of the conduit end as a function of the location of the source. In another method, the quality of the bottoming of a conduit end is determined by applying energy into the conduit structure, detecting reflected or returned energy from the conduit end and determining the quality of bottoming of the conduit end as a function of the reflected energy signal strength. Both methods may be used alone or in combination with each other or other analysis, and both methods may optionally utilize the above-described noise filtering and correlation techniques.

As some of the many available alternatives, the electronics 16 may be incorporated into any suitable package for use in the desired application and environment. For example, the electronics 16 including the source 12 may be incorporated into a device or tool that also is used as a conventional gap gauge. The electronics 16 may produce an output of any desired format, and for example, could simply be a light that indicates a go/no go result of the bottoming of the tube end. The electronics may also incorporate intelligent rules based software such as neural nets for calibration and/or analysis and may include the above described noise filtering and correlation techniques.

The source 12 may alternatively be configured to apply the input energy into a component of the fluid coupling, rather than or in addition to the conduit. This would only require a simply reconfiguration of the interface geometry of the base 20 for example. Depending on the surface for mounting, the base 20 may even be unnecessary. For example, the source 12 may apply the input energy into the fitting body B, such as at the head or neck of the fitting body.

Still further, the present invention may be used to determine, separately or in combination with the conduit end position, other evaluations of the fitting assembly. As described herein above, the present invention may be used to determine the position and abutment characteristics of the conduit end. The invention may also be used to determine the position and characteristics of other normal deformations and structural variations of the conduit such as are associated with the fluid coupling, as such conditions may also produce reflected energy. For example, but not limited thereto, the invention may be used to detect the presence and/or location of the bite or tube indentation or compression caused by one or more of the ferrules. By determining that the selected condition is positioned properly and has the desired quality, the user may know that the fitting assembly has been properly completed, such as knowing that the ferrules are correctly installed and pulled up. Absence of such signals may indicate improper assembly or pull-up.

In another embodiment, the invention is a tool that can be used to check both the correctness of the geometric pull-up and the internal integrity of a twin-ferrule tube fitting. Using ultrasonic sensor(s) and a microprocessor embedded with advanced mathematical software, the tool will be able to detect if the tubing is fully bottomed against the tube bore shoulder (i.e. correct tube installation, See FIG. 4). The main advantage of this design is to provide an alternative that is non-destructive (e.g. actual disassembly/re-assembly of fitting) and low in cost (relative to X-raying fitting connections) and greatly reduces the potential for the product to be installed improperly.

Figure 5:
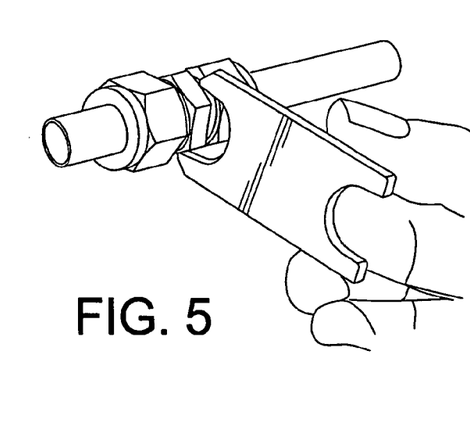
FIG. 5 is an alternative embodiment wherein a source and/or an analyzer is integrated with a hand-held tool, such as a gap gauge.
Figure 6:
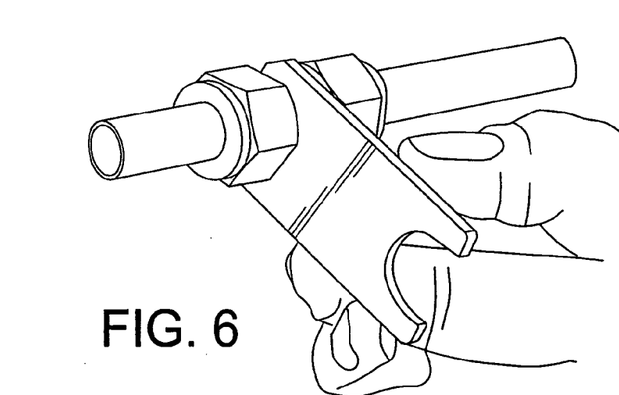
FIG. 6 is the tool shown in FIG. 5 implemented through the fitting neck.
Figure 7:
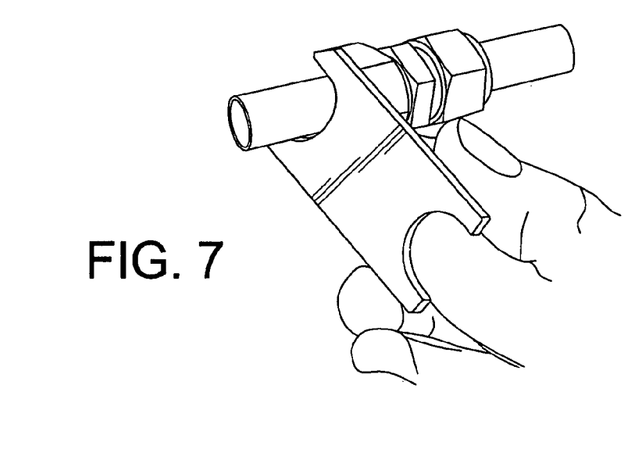
FIG. 7 is the tool shown in FIG. 6 implemented through the tube and nut.
Figure 8:
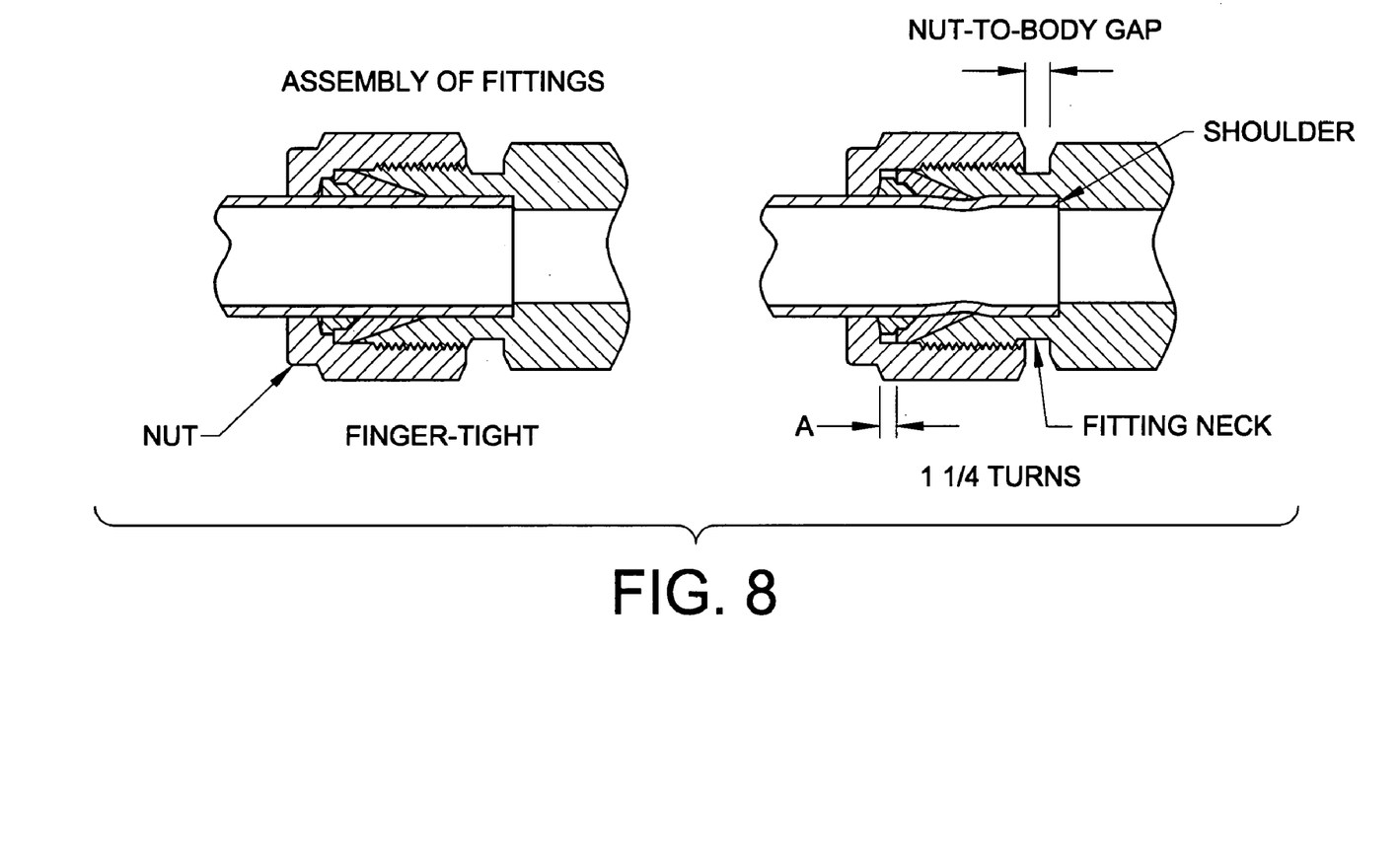
FIG. 8 is an assembly of fittings wherein the tool of FIG. 5 can be implemented.

The hand-held tool shown in FIGS. 5-7 verifies correct geometric pull-up, as shown in FIG. 8 (i.e. 1-¼ turns past finger-tight by gauging the "nut-to-body" gap) and detects if the tubing is fully bottomed against the tube bore shoulder. Further, use of the tool does not require the fitting to be disassembled and thereby eliminates the need to use of X-ray equipment. The tube-gripping portion of the tool verifies the correctness of the geometric pull-up by gauging the "nut-to-body" gap. The nut-to body gap is held consistent due to tightly toleranced critical dimensions placed on the nut, ferrules, and fitting body. This feature is designed such that the tool cannot fit in between the nut and the fitting body when the required "nut-to-body" gap is reached. As such, the tool acts as a conventional gap gauge, as disclosed in US Pat. No. 3,287,813, the disclosure of which is fully incorporated herein by reference. The back end of the tool detects if the tubing is fully bottomed against the tube bore shoulder, located inside the fitting body (i.e. correct tube installation). Using one or more ultrasonic sensors and a microprocessor embedded with advanced mathematical software, the tool can selectively scan critical internal features of the fitting body and components and notify the user, audibly or visually, if the tubing is correctly installed. The tool may scan the fitting using any of the methods described herein above.

The invention has been described with reference to the preferred embodiment. Modifications and alterations will occur to others upon a reading and understanding of this specification. It is intended to include all such modifications and alterations insofar as they come within the scope of the appended claims or the equivalents thereof.

Having thus described the invention, we claim:

1. A method for evaluating a fitting of the type having a conduit assembled at one end to a fitting comprising a body, a nut, and at least one ferrule, the method comprising the steps of:

assembling a fitting body, a fitting nut and at least one ferrule onto an end of a conduit;

applying mechanical energy into the conduit at a reference position;

detecting at said reference position reflected mechanical energy; and determining, as a function of said reflected mechanical energy, axial position of the conduit end in the fitting relative to the reference position.

2. The method of claim 1, wherein the step of applying mechanical energy into the conduit at a reference position includes the step of positioning a source of the mechanical energy against a fitting surface.

3. The method of claim 1, wherein the step of applying mechanical energy into the conduit at a reference position includes the step of positioning a source of the mechanical energy against a face of the nut.

4. The method of claim 1, further comprising the step of tightening the fitting to a pulled-up condition prior to applying said mechanical energy.

5. The method of claim 1, further comprising the step of comparing the axial position of the conduit end, relative to the reference position, to corresponding test data for a properly pulled-up fitting assembly.

6. The method of claim 1 wherein the mechanical energy is applied into the neck of the fitting body.

7. A method for evaluating position of a conduit in a fluid coupling, comprising the steps of:

assembling a body with an unthreaded end of a conduit;

forming a fluid tight seal and grip against an outer surface of the conduit end;

applying mechanical energy waves at a first location that is axially spaced from said conduit end;

receiving return portions of said energy waves; and determining axial position of said conduit end in the body relative to said first location as a function of said received return portions of said energy waves.

8. The method of claim 7 wherein the step of applying energy waves comprises the step of applying ultrasonic energy shear waves.

9. The method of claim 7 wherein said energy waves are transient.

10. The method of claim 7 wherein said determining step comprises converting said received return portions of said energy waves into corresponding electrical signals and applying noise reduction to said electrical signals.

11. The method of claim 7 wherein said determining step comprises correlation analysis on said received return portions.

12. The method of claim 7 comprising the step of applying said energy waves at two or more different radial positions about the conduit end at said first location.

13. The method of claim 7 comprising the step of correlating and filtering said received return portions using a Morlet wavelet correlation function.

14. The method of claim 7 wherein the fluid coupling comprises a fitting body, fitting nut and at least one ferrule, and the method further comprises applying the mechanical energy waves into the neck of a fitting body.

15. The method of claim 7, wherein the step of applying mechanical energy waves includes the step of positioning a source of the mechanical energy waves against a coupling member.

16. The method of claim 7, wherein the step of applying mechanical energy waves includes the step of positioning a source of the mechanical energy against a face of a coupling nut.

17. The method of claim 7, further comprising the step of comparing an axial position of the conduit end, relative to said first position, to corresponding test data for a known properly pulled-up fitting assembly.

18. The method of claim 7 wherein the step of forming a fluid tight seal and grip against an outer surface of the conduit end includes the step of applying compression of a gripping device against an outer surface of the conduit end.

19. The method of claim 18 wherein said step of applying compression produces an indentation in the conduit end.

20. The method of claim 7 wherein said determining step includes quality of contact between the end face of the conduit and an internal surface of the fitting body and is selected from a group consisting of: contact surface area, gap between the conduit end face and said internal surface, and square alignment of the conduit end face and said internal surface.

21. A method for evaluating a fitting of the type having a conduit assembled at one end to a fitting comprising a body, a nut, and at least one ferrule, the method comprising the steps of:

inserting an end of an unthreaded conduit into a fitting body;

forming a fluid tight seal and grip against an outer surface of the conduit end;

applying mechanical energy at a reference position that is axially spaced from the conduit end;

detecting reflected mechanical energy; and determining, as a function of said reflected mechanical energy, axial position of the conduit end in the fitting body relative to the reference position.

22. The method of claim 21 wherein said determining step includes quality of contact between the end face of the conduit and an internal surface of the fitting body and is selected from a group consisting of: contact surface area, gap between the conduit end face and said internal surface, and square alignment of the conduit end face and said internal surface.

* * * * *